United States Patent [19]
Yamada et al.

[11] Patent Number: 5,877,840
[45] Date of Patent: Mar. 2, 1999

[54] BINOCULAR VIEW FUNCTION INSPECTING APPARATUS AND INSPECTING METHOD

[75] Inventors: Teruhiro Yamada, Katano; Satoshi Takemoto, Hirakata; Takashi Ikeda, Higashiosaka, all of Japan; Toshio Obase, Cupertino, Calif.

[73] Assignee: Sanyo Electric Co., Ltd., Osaka, Japan

[21] Appl. No.: 919,765

[22] Filed: Sep. 16, 1997

[30] Foreign Application Priority Data

Sep. 20, 1996 [JP] Japan .................................. 8-250449
May 15, 1997 [JP] Japan .................................. 9-125431

[51] Int. Cl.⁶ ................................................ A61B 3/10
[52] U.S. Cl. ........................ 351/201; 351/202; 351/240
[58] Field of Search .................................. 351/201, 202, 351/200, 203, 240, 246, 211, 209

[56] References Cited

U.S. PATENT DOCUMENTS

| | | | |
|---|---|---|---|
| 4,057,054 | 11/1977 | Giannone | 351/203 |
| 4,961,640 | 10/1990 | Irlen | 351/44 |
| 5,235,361 | 8/1993 | Suoer | 351/240 |

*Primary Examiner*—George Manuel
*Attorney, Agent, or Firm*—Nikaido, Marmelstein, Murray & Oram LLP

[57] ABSTRACT

A reference image and an index image are displayed on a three-dimensional display device with either one of the images taken as a left eye image and the other image taken as a right eye image. When a movement command to move a display position of the index image is inputted by a person to be inspected in order that a predetermined reference position of the reference image and the display position of the index image coincide with each other, the display position of the index image is moved on the basis of the movement command. The amount of deviation of the index image from the reference position of the reference image is calculated by the person to be inspected visually recognizing that the reference position of the reference image and the display position of the index image coincide with each other when confirmation input indicating that the person to be inspected visually recognizes the coincidence is provided by the person to be inspected.

17 Claims, 18 Drawing Sheets

LEFT EYE REDUCED IMAGE    RIGHT EYE REDUCED IMAGE

BINOCULAR VIEW FUNCTION INSPECTING APPARATUS AND INSPECTING METHOD

BACKGROUND OF THE INVENTION

1. Field of the Invention

The present invention relates to a binocular view function inspecting apparatus and a binocular view function inspecting method for measuring a binocular view function and particularly measuring a self-conscious strabismic angle of heterophoria.

2. Description of the Prior Art

Examples of a method of measuring a self-conscious strabismic angle of heterophoria include a so-called Maddox test. In this test, an apparatus called a Maddox wing having a partition plate for separating a left eye field of view and a right eye field of view so that a horizontal scale 101 shown in FIG. 23 and a vertical bar 102 shown in FIG. 24 are respectively seen with the left eye and the right eye. When a person to be inspected is normal, the vertical bar 102 is so seen as to coincide with the reference position "0" of the horizontal scale 101, as shown in FIG. 25. When the person to be inspected has a squint, the vertical bar 102 is seen in a position deviating from the reference position "0" of the horizontal scale 101, as shown in FIG. 26.

In this test, the person to be inspected answers a position, where the vertical bar 102 is seen, on the horizontal scale 101, and an inspecting person judges whether or not the person to be inspected is normal on the basis of the answer. Therefore, the amount of deviation of the vertical bar 102 from the reference position of the horizontal scale 101 cannot be objectively or automatically measured. That is, the degree of strabismus cannot be objectively or automatically measured.

SUMMARY OF THE INVENTION

An object of the present invention is to provide a binocular view function inspecting apparatus and a binocular view function inspecting method, in which the degree of strabismus can be objectively measured.

Another object of the present invention is to provide a binocular view function inspecting apparatus and a binocular view function inspecting method, in which the degree of strabismus can be automatically measured.

Still another object of the present invention is to provide a strabismus correcting apparatus and a strabismus correcting method, in which strabismus can be corrected.

A binocular view function inspecting apparatus according to the present invention is characterized by comprising display means for displaying a reference image and an index image on a three-dimensional display (3D) device with either one of the images taken as a left eye image and the other image taken as a right eye image, first input means for causing a person to be inspected to input a movement command to move a display position of the index image in order that a predetermined reference position of the reference image and the display position of the index image coincide with each other, index image movement means for moving the display position of the index image on the basis of the movement command from the first input means, second input means for causing the person to be inspected to provide, when the person to be inspected visually recognizes that the reference position of the reference image and the display position of the index image coincide with each other, confirmation input indicating that the person to be inspected visually recognizes the coincidence, and calculation means for calculating the amount of deviation of the index image from the reference position of the reference image when the confirmation input is provided.

In the binocular view function inspecting apparatus according to the present invention, the amount of deviation of the index image from the reference position of the reference image can be objectively and automatically measured.

It is preferable to provide judgment means for judging whether or not the person to be inspected is normal on the basis of the amount of deviation calculated by the calculation means, and reporting means for reporting the results of the judgment by the judgment means to an inspecting person. Examples of the reporting means include one for displaying the results of judgment on a display device for an inspecting person, and one for outputting the results of judgment by a printer. The amount of deviation calculated by the calculation means may be displayed on the display device for an inspecting person, and may be outputted by the printer. Further, the amount of deviation calculated by the calculation means may be stored in a storage device such as a hard disk. Consequently, the results of inspection corresponding to a plurality of persons to be inspected can be utilized as a data base.

A binocular view function inspecting method according to the present invention is characterized by comprising a first step of displaying a reference image and an index image on a 3D display device with either one of the images taken as a left eye image and the other image taken as a right eye image, a second step of causing a person to be inspected to input a movement command to move a display position of the index image in order that a predetermined reference position of the reference image and the display position of the index image coincide with each other, a third step of moving the display position of the index image on the basis of the inputted movement command, a fourth step of causing the person to be inspected to provide, when the person to be inspected visually recognizes that the reference position of the reference image and the display position of the index image coincide with each other, confirmation input indicating that the person to be inspected visually recognizes the coincidence, and a fifth step of calculating the amount of deviation of the index image from the reference position of the reference image when the confirmation input is provided.

In the binocular view function inspecting method according to the present invention, the amount of deviation of the index image from the reference position of the reference image can be objectively and automatically measured.

It is preferable to provide a six step of judging whether or not the person to be inspected is normal on the basis of the amount of deviation calculated in the fifth step, and a seventh step of reporting the results of the judgment in the sixth step to an inspecting person.

Examples of a method of reporting the results of the judgment in the sixth step to the inspecting person include a method of displaying the results of judgment on a display device for an inspecting person and a method of outputting the results of judgment by a printer. The amount of deviation calculated in the fifth step may be displayed on the display device for an inspecting person, and may be outputted by the printer. Further, the amount of deviation calculated in the fifth step may be stored in a storage device such as a hard disk. Consequently, the results of inspection corresponding to a plurality of persons to be inspected can be utilized as a data base.

A computer readable recording medium on which a binocular view function inspecting program is recorded according to the present invention is characterized in that the program causes a computer to carry out the steps of displaying a reference image and an index image on a 3D display device with either one of the images taken as a left eye image and the other image taken as a right eye image, moving a display position of the index image, when a movement command to move the display position of the index image is inputted by a person to be inspected in order that a predetermined reference position of the reference image and the display position of the index image coincide with each other, on the basis of the movement command, and calculating the amount of deviation of the index image from the reference position of the reference image by the person to be inspected visually recognizing that the reference position of the reference image and the display position of the index image coincide with each other when confirmation input indicating that the person to be inspected visually recognizes the coincidence is provided by the person to be inspected.

A strabismus correcting apparatus according to the present invention is characterized by comprising strabismic angle measurement means for measuring information relating to the strabismic angle of a person to be inspected, and strabismus correcting means for displaying a strabismus correcting image comprising a left eye image and a right eye image on a 3D display device on the basis of the information relating to the strabismic angle measured by the strabismic angle measurement means, the strabismus correcting means comprising means for displaying the strabismus correcting image comprising the left eye image and the right eye image which have an amount of deviation corresponding to the strabismic angle of the person to be inspected on the 3D display device, and means for gradually decreasing the amount of deviation between the left eye image and the right eye image in the strabismus correcting image displayed on the 3D display device.

Examples of the strabismic angle measurement means include one comprising display means for displaying a reference image and an index image on the 3D display device with either one of the images taken as a left eye image and the other image taken as a right eye image, first input means for causing the person to be inspected to input a movement command to move a display position of the index image in order that a predetermined reference position of the reference image and the display position of the index image coincide with each other, index image movement means for moving the display position of the index image on the basis of the movement command from the first input means, second input means for causing the person to be inspected to provide, when the person to be inspected visually recognizes that the reference position of the reference image and the a display position of the index image coincide with each other, confirmation input indicating that the person to be inspected visually recognizes the coincidence, and calculation means for calculating the amount of deviation of the index image from the reference position of the reference image when the confirmation input is provided, to obtain information relating to the strabismic angle of the person to be inspected.

It is preferable to use a moving image as the strabismus correcting image.

A strabismus correcting method according to the present invention is characterized by comprising a strabismic angle measuring step of measuring information relating to the strabismic angle of a person to be inspected, and a strabismus correcting step of displaying a strabismus correcting image comprising a left eye image and a right eye image on a 3D display device on the basis of the information relating to the strabismic angle measured by the strabismic angle measurement step, the strabismus correcting step comprising the step of displaying the strabismus correcting image comprising the left eye image and the right eye image which have an amount of deviation corresponding to the strabismic angle of the person to be inspected on the 3D display device, and the step of gradually decreasing the amount of deviation between the left eye image and the right eye image in the strabismus correcting image displayed on the 3D display device.

Examples of the strabismic angle measuring step include one comprising a first step of displaying a reference image and an index image on the 3D display device with either one of the images taken as a left eye image and the other image taken as a right eye image, a second step of causing the person to be inspected to input a movement command to move a display position of the index image in order that a predetermined reference position of the reference image and the display position of the index image coincide with each other, a third step of moving the display position of the index image on the basis of the movement command from the first input means, a fourth step of causing the person to be inspected to provide, when the person to be inspected visually recognizes that the reference position of the reference image and the display position of the index image coincide with each other, confirmation input indicating that the person to be inspected visually recognizes the coincidence, and a fifth step of calculating the amount of deviation of the index image from the reference position of the reference image when the confirmation input is provided, to obtain information relating to the strabismic angle of the person to be inspected.

It is preferable to use a moving image as the strabismus correcting image.

A computer readable recording medium on which a strabismus correcting program is recorded according to the present invention is characterized in that the program causes a computer to carry out a strabismic angle measuring step of measuring information relating to the strabismic angle of a person to be inspected, and a strabismus correcting step of displaying a strabismus correcting image comprising a left eye image and a right eye image on a 3D display device on the basis of the information relating to the strabismic angle measured by the strabismic angle measuring step, the strabismus correcting step comprising the step of displaying the strabismus correcting image comprising the left eye image and the right eye image which have an amount of deviation corresponding to the strabismic angle of the person to be inspected on the 3D display device, and the step of gradually decreasing the amount of deviation between the left eye image and the right eye image in the strabismus correcting image displayed on the 3D display device.

Examples of the strabismic angle measuring step include one comprising the steps of displaying a reference image and an index image on a 3D display device with either one of the images taken as a left eye image and the other image taken as a right eye image, moving a display position of the index image, when a movement command to move the display position of the index image is inputted by a person to be inspected in order that a predetermined reference position of the reference image and the display position of the index image coincide with each other, on the basis of the movement command, calculating the amount of deviation of the index image from the reference position of the reference image by the person to be inspected visually recognizing that the reference position of the reference image and the display position of the index image coincide with each other when confirmation input indicating that the person to be inspected visually recognizes the coincidence is provided by the person to be inspected.

It is preferable to use a moving image as the strabismus correcting image.

The foregoing and other objects, features, aspects and advantages of the present invention will become more apparent from the following detailed description of the present invention when taken in conjunction with the accompanying drawings.

DETAILED DESCRIPTION OF THE PREFERRED EMBODIMENTS

Figure 1:
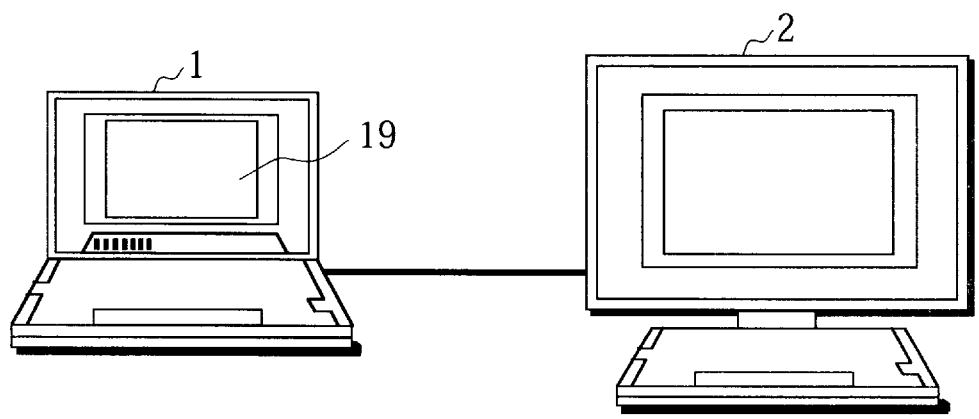
FIG. 1 is a diagram showing the appearance of a binocular view function inspecting apparatus.

Referring now to the drawings, embodiments of the present invention will be described.

[1] Description of Binocular View Function Inspecting Apparatus

FIG. 1 illustrates the appearance of a binocular view function inspecting apparatus.

The binocular view function inspecting apparatus is constituted by a personal computer 1 operated by an inspecting person and a three-dimensional display device (3D display device) 2 providing an image for inspecting a binocular view function to a person to be inspected. As the personal computer 1, a so-called notebook-sized personal computer comprising a two-dimensional display (2D display) 19 is used in this example. An example of the 3D display device 2 is one of a parallax barrier type.

Figure 2:
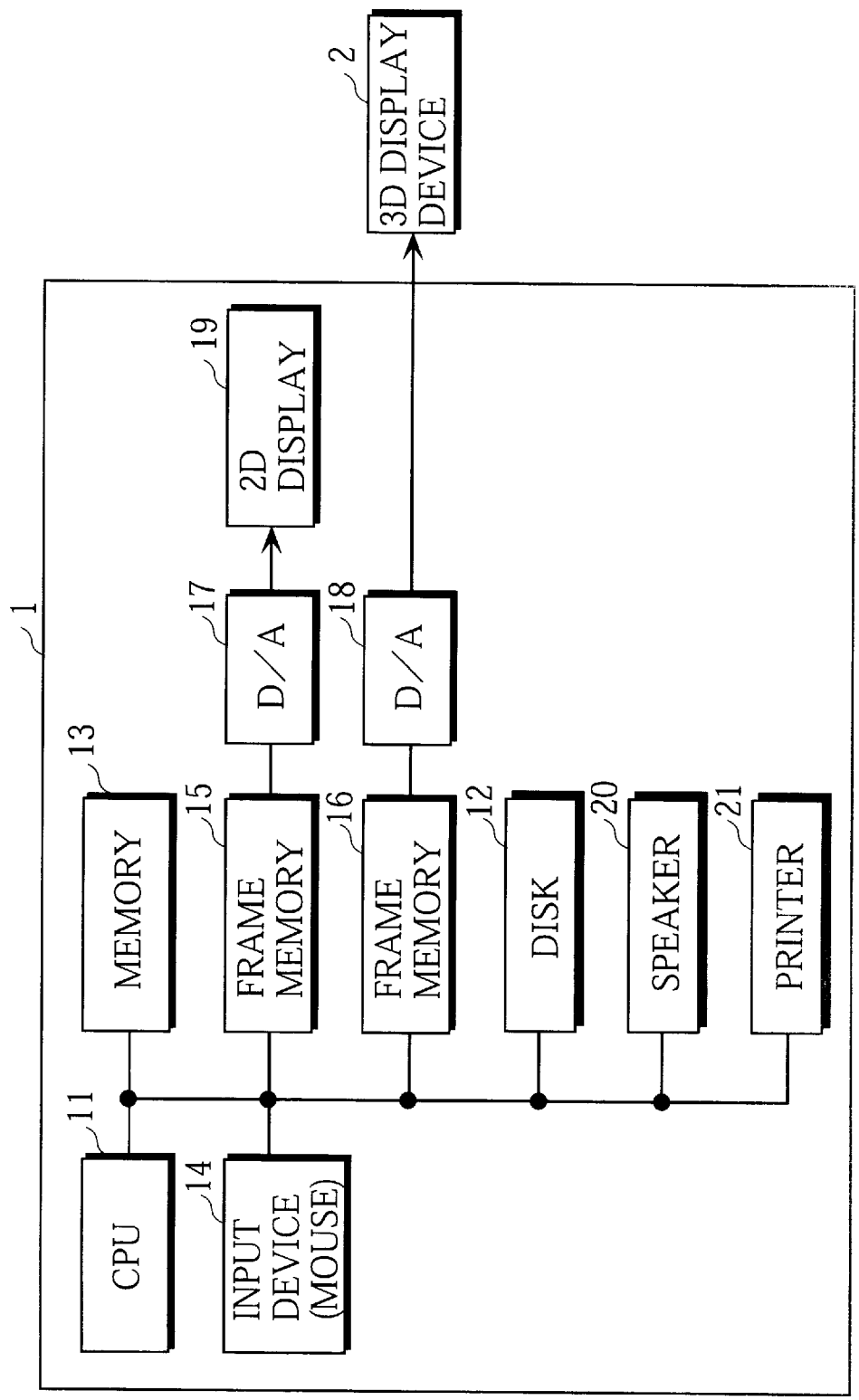
FIG. 2 is a block diagram showing the construction of a binocular view function inspecting apparatus.

FIG. 2 illustrates the construction of the binocular view function inspecting apparatus.

A personal computer 1 is controlled by a CPU 11. Connected to the CPU 11 are a hard disk 12 storing its program and the like and a memory 13 storing necessary data. Further, an input device 14 including a mouse, a speaker 20 and a printer 21 are connected to the CPU 11.

Furthermore, a first frame memory 15 and a second frame memory 16 are connected to the CPU 11. The first frame memory 15 is connected to a 2D display 19 through a D/A (digital-to-analog) converter 17. The second frame memory 16 is connected to a 3D display device 2 through a D/A converter 18.

Figure 3:
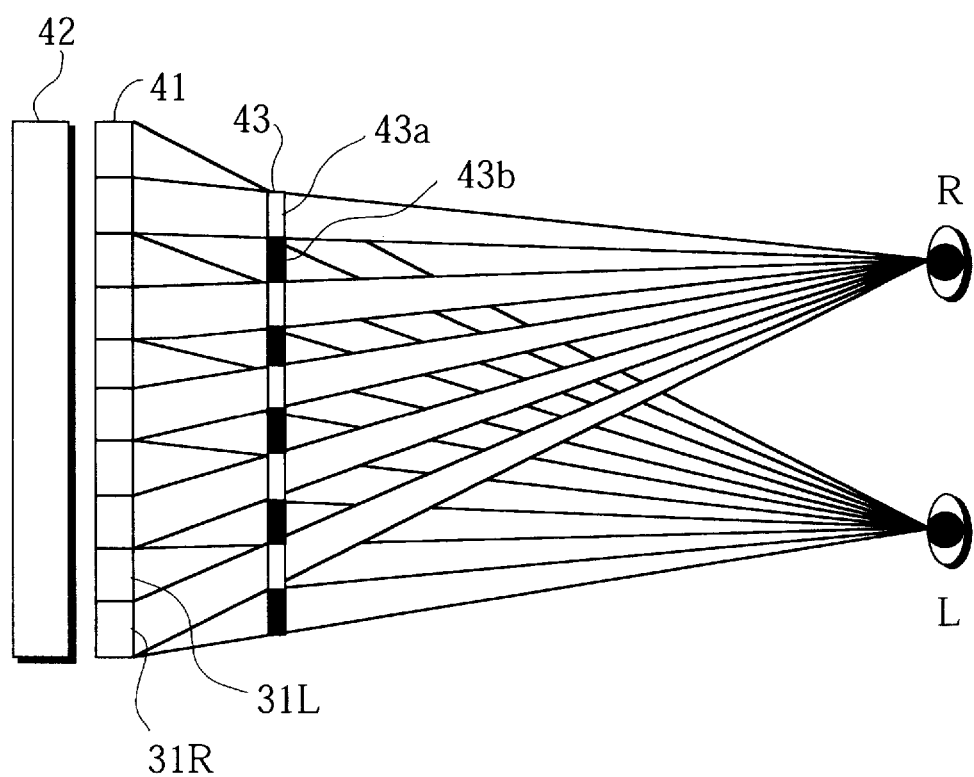
FIG. 3 is a schematic view showing the construction of a display section in a 3D display device.

FIG. 3 illustrates the construction of a display section in the 3D display device 2.

Figure 4:
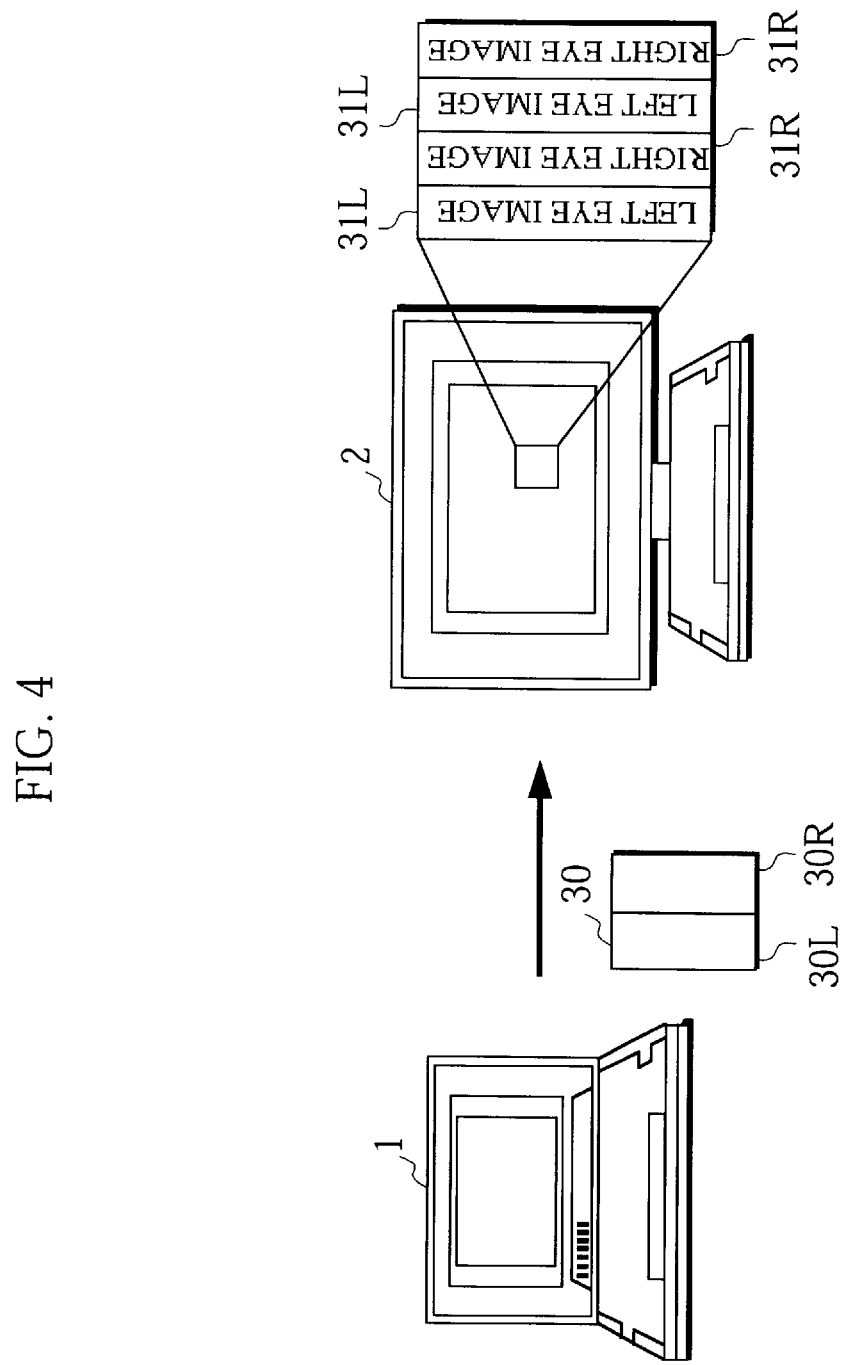
FIG. 4 is a schematic view showing an image fed to a 3D display device from a personal computer and an image displayed on the 3D display device.

Image information 30 comprising a left eye reduced image 30L obtained by reducing an original left eye image to one-half in the horizontal direction and a right eye reduced image 30R obtained by reducing an original right eye image to one-half in the horizontal direction is sent to the 3D display device 2 from the personal computer 1, as shown in FIG. 4. The 3D display device 2 respectively decomposes the left eye reduced image and the right eye reduced image which are sent into longwise strip-shaped images, alternately arrange the left eye strip-shaped images 31L and the right eye strip-shaped images 31R in the horizontal direction and displays the images on a liquid crystal panel 41, as shown in FIGS. 3 and 4.

As shown in FIG. 3, a back light 42 is disposed behind the liquid crystal panel 41. A parallax barrier 43 in which apertures 43a and barriers 43b are alternately arranged in the horizontal direction is disposed ahead of the liquid crystal panel 41. A person to be inspected views an image on the liquid crystal panel 41 through the parallax barrier 43, so that only the left eye strip-shaped images and only the right eye strip-shaped images are respectively seen with the left eye L and the right eye R.

Figure 5:
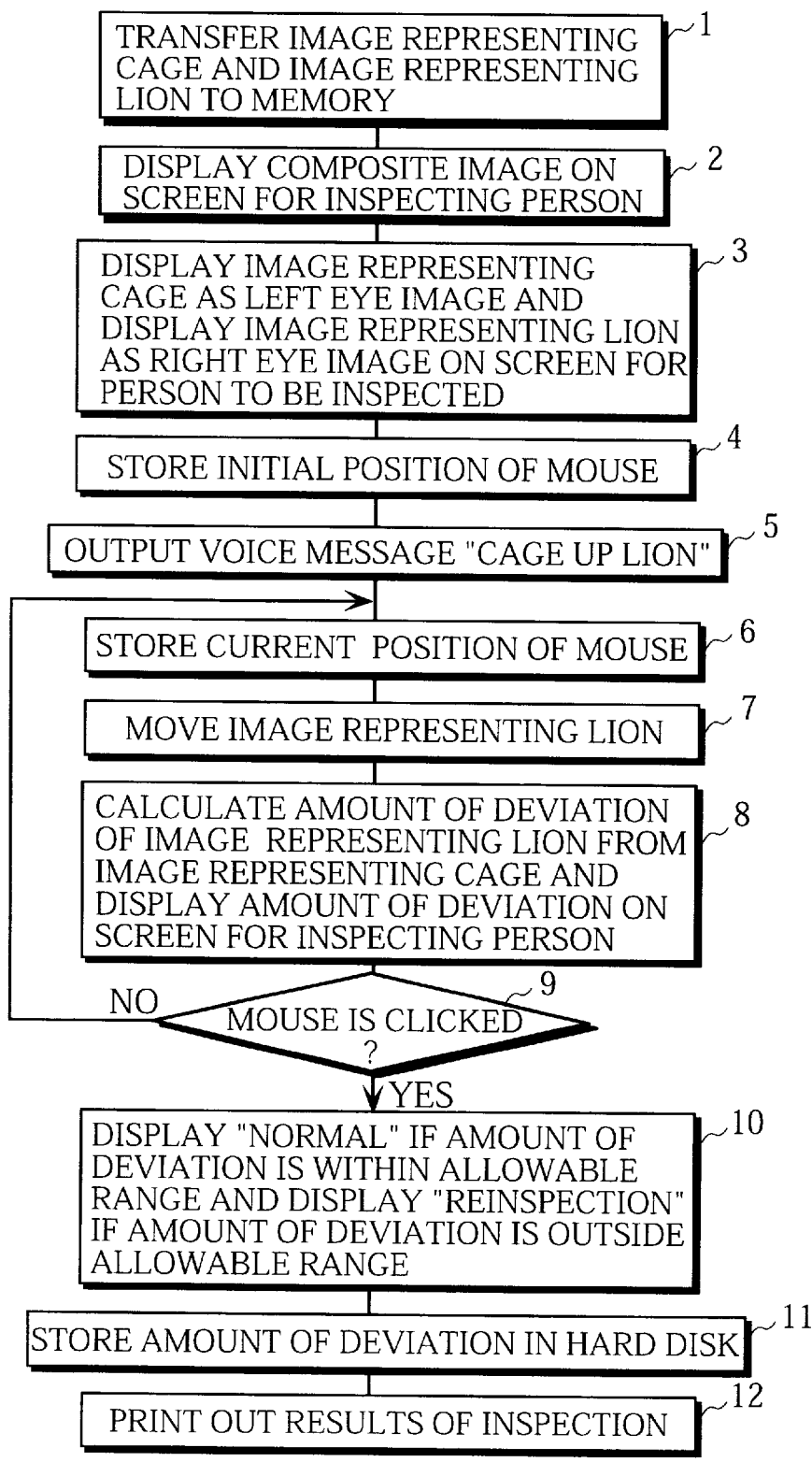
FIG. 5 is a flow chart showing the procedure for inspection processing of a binocular view function.

FIG. 5 shows the procedure for inspection processing of a binocular view function.

Figure 6:
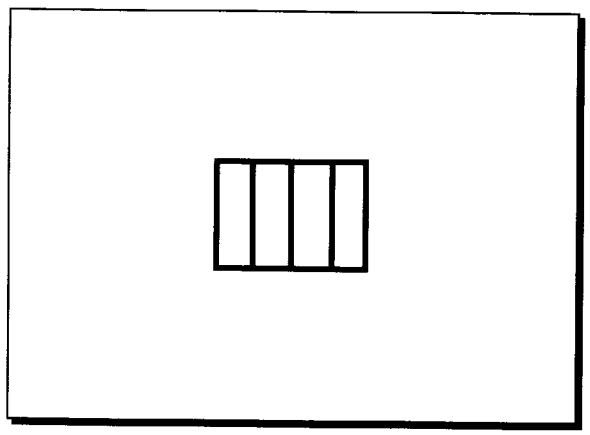
FIG. 6 is a schematic view showing an image representing a cage which is a reference image.
Figure 7:
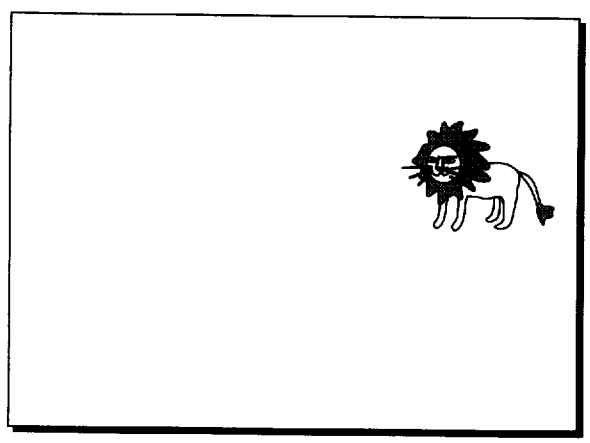
FIG. 7 is a schematic view showing an image representing a lion which is an index image.
Figure 8:
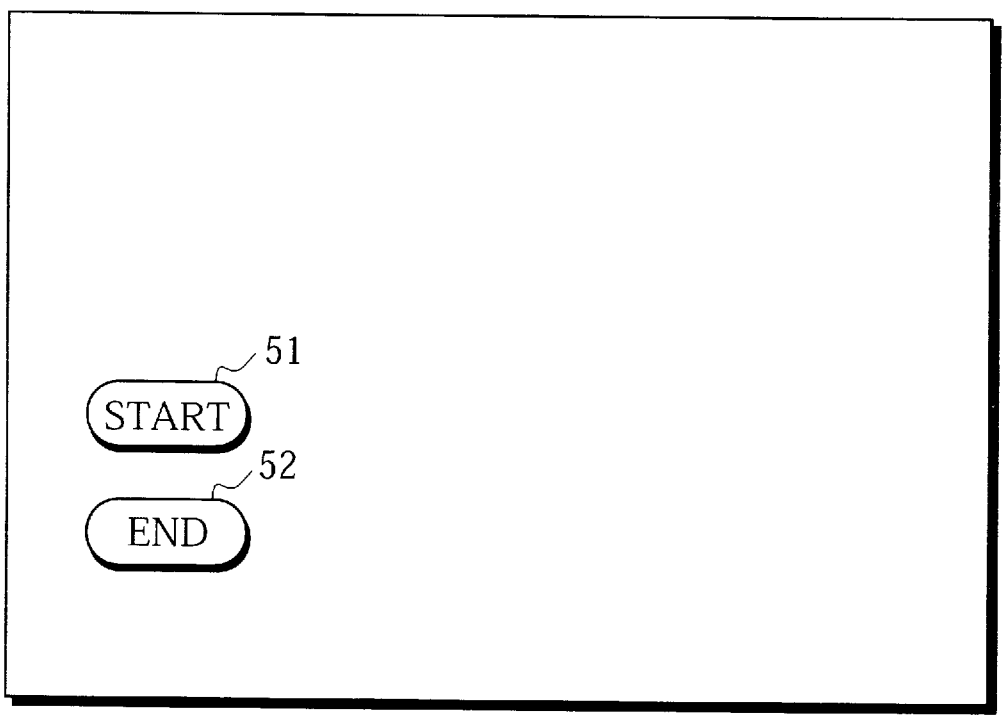
FIG. 8 is a schematic view showing one example of an initial screen in a case where a binocular view function is inspected.

An image representing a cage serving as a reference image shown in FIG. 6 and an image representing a lion serving as an index image shown in FIG. 7 are stored in the hard disk 12. FIG. 8 illustrates one example of an initial screen displayed on the 2D display 19 (hereinafter referred to as a screen for an inspecting person). A start button 51 and an end button 52 are displayed on the initial screen.

Figure 9:
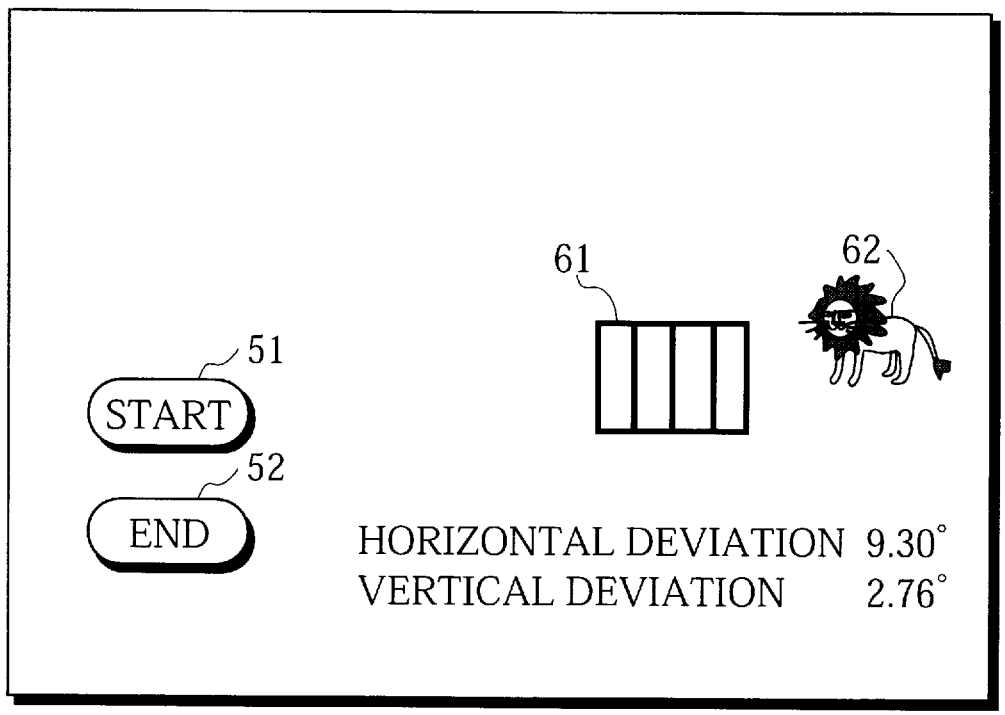
FIG. 9 illustrates one example of a screen for an inspecting person immediately after starting inspection of a binocular view function.

When the start button 51 is pushed, the image representing the cage and the image representing the lion are read out from the hard disk 12, and are stored in the memory 13 (step 1). Their composite image is sent to the 2D display 19 through the frame memory 15 and the D/A converter 17, and is displayed on the 2D display 19 (step 2). One example of the image is illustrated in FIG. 9.

In this example, an image representing a cage 61 and an image representing a lion 62 are displayed in addition to the start button 51 and the end button 52, and their horizontal deviation and their vertical deviation are displayed.

Figure 10:
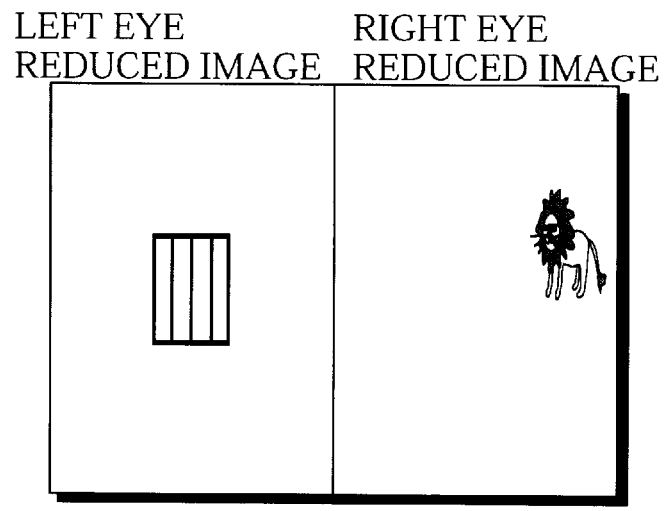
FIG. 10 is a schematic view showing a left eye reduced image corresponding to an image representing a cage displayed on the screen for an inspecting person shown in FIG. 9 and a right eye reduced image corresponding to an image representing a lion displayed on the screen for an inspecting person shown in FIG. 9.

On the other hand, the image representing the cage and the image representing the lion which are stored in the memory 13 are taken as a left eye image and a right eye image and are reduced to one-half in the horizontal direction, respectively, to produce an image corresponding to one frame. One example of a left eye reduced image and a right eye reduced image respectively corresponding to the images representing the cage and the lion which are displayed on the screen for an inspecting person shown in FIG. 9 is illustrated in FIG. 10. The produced image corresponding to one frame is sent to the 3D display device 2 through the frame memory 16 and the D/A converter 18.

The 3D display device 2 respectively decomposes the left eye reduced image and the right eye reduced image which are sent into longwise strip-shaped images, alternately arranges the left eye strip-shaped images and the right eye strip-shaped images in the horizontal direction and displays the images on the liquid crystal panel 41 (hereinafter referred to as a screen for a person to be inspected) (step 3). Consequently, the same images as the images displayed on the screen for an inspecting person, that is, the image representing the cage and the image representing the lion are displayed on the screen for a person to be inspected. Only the image representing the cage and only the image representing the lion are respectively seen with the left eye and the right eye of a person to be inspected.

Furthermore, the initial position of the mouse is stored in the memory 13 (step 4). Thereafter, a voice message "Cage a lion" is outputted from the speaker 20 (step 5).

An operator so operates the mouse (included in the input device 14) that the lion is caged, and clicks the mouse when the lion has been caged.

When the mouse is operated, the current position of the mouse is stored in the memory 13 (step 6). The image representing the lion is moved on the screen for an inspecting person and the screen for a person to be inspected on the basis of the direction in which the mouse is moved and the amount of movement thereof (step 7). A new image displayed on the screen for an inspecting person and a new image sent to the 3D display device 2 are produced on the basis of the image representing the cage and the image representing the lion which are stored in the memory 13.

The amount of deviation (the amount of deviation in the horizontal direction and the amount of deviation in the vertical direction) between the image representing the cage and the image representing the lion is calculated on the basis of the direction in which the mouse is moved and the amount of movement thereof, and the calculated amount of deviation is displayed on the screen for an inspecting person (step 8).

Figure 11:
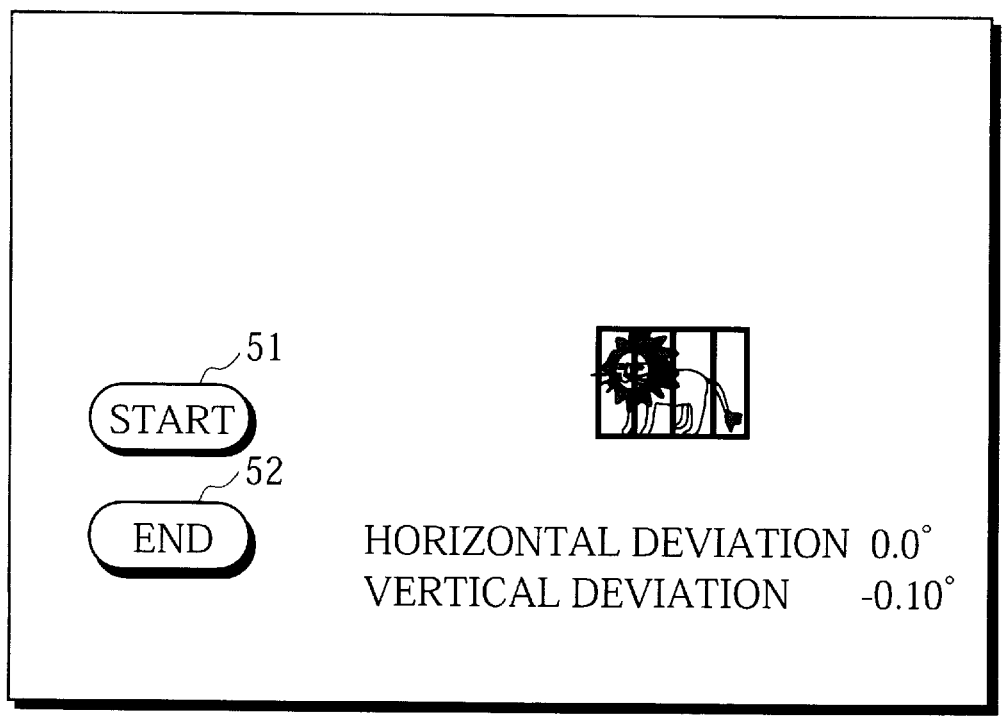
FIG. 11 illustrates one example of a screen for an inspecting person in a case where a mouse is clicked by a person to be inspected.
Figure 12:
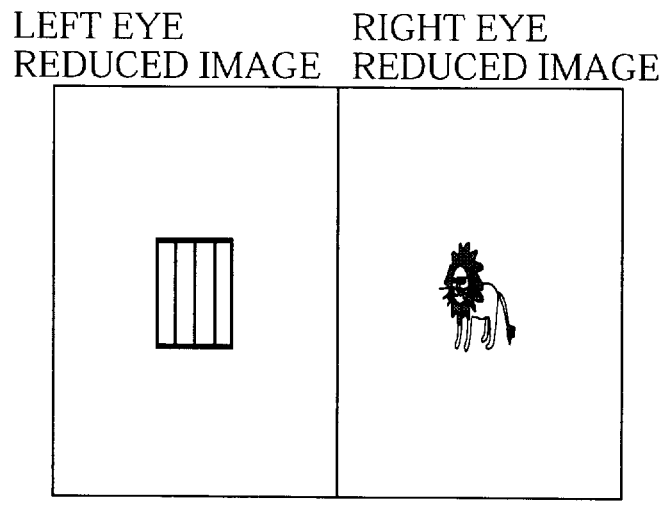
FIG. 12 is a schematic view showing a left eye reduced image corresponding to an image representing a cage displayed on the screen for an inspecting person shown in FIG. 11 and a right eye reduced image corresponding to an image representing a lion displayed on the screen for an inspecting person shown in FIG. 11.

Until the mouse is clicked, the processing in the steps 6 to 8 is repeatedly performed. When the mouse is clicked, the answer is in the affirmative in the step 9, after which the program proceeds to the step 10. One example of the screen for an inspecting person in a case where the mouse is clicked is shown in FIG. 11. Further, a left eye reduced image and a right eye reduced image respectively corresponding to the images representing the cage and the lion which are displayed on the screen for an inspecting person shown in FIG. 11 are illustrated in FIG. 12.

In the step 10, "normal" is displayed if the amount of deviation between the image representing the cage and the image representing the lion is within an allowable range, while "reinspection" is displayed on the screen for an inspecting person if it is outside the allowable range. Further, the amount of deviation corresponding to the person to be inspected is stored in the hard disk 12 (step 11), and the results of the inspection is outputted by the printer 21 (step 12).

Although in the above-mentioned embodiment, description was made of an example in which the image representing the cage serving as a reference image is taken as a left eye image, and the image representing the lion serving as an index image which is moved by the mouse is taken as a right eye image, it is preferable to provide both such an inspection mode and such an inspection mode that the image representing the cage is taken as a right eye image and the image representing the lion which is moved by the mouse is taken as a left eye image.

Figure 13:
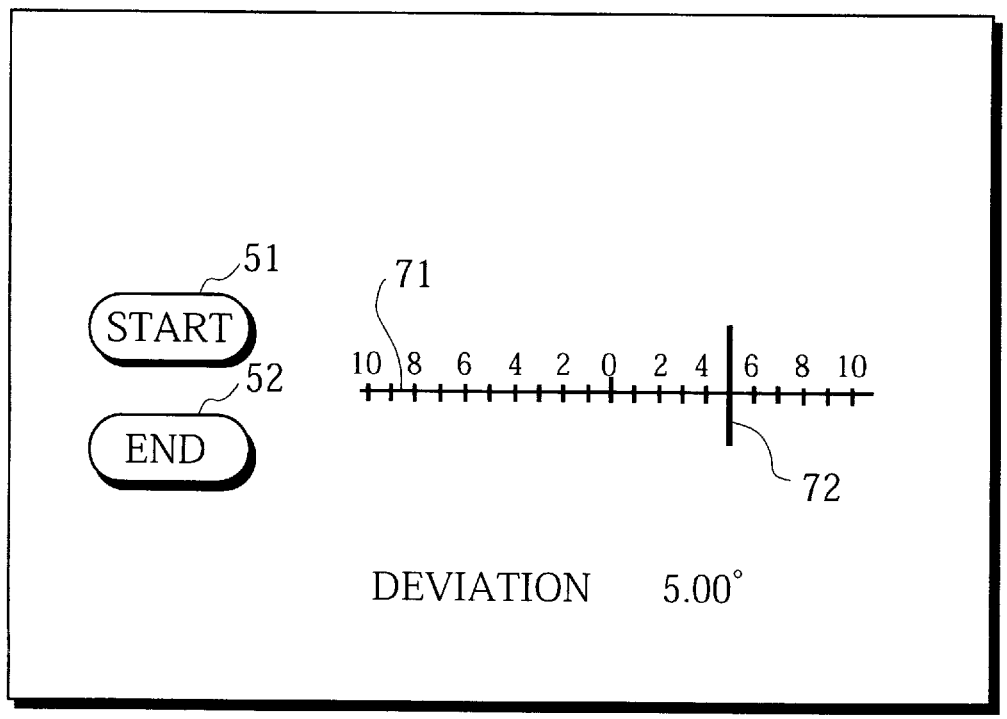
FIG. 13 illustrates one example of a screen for an inspecting person in a case where an image representing a horizontal scale is used as a reference image, and an image representing a vertical bar is used as an index image.
Figure 14:
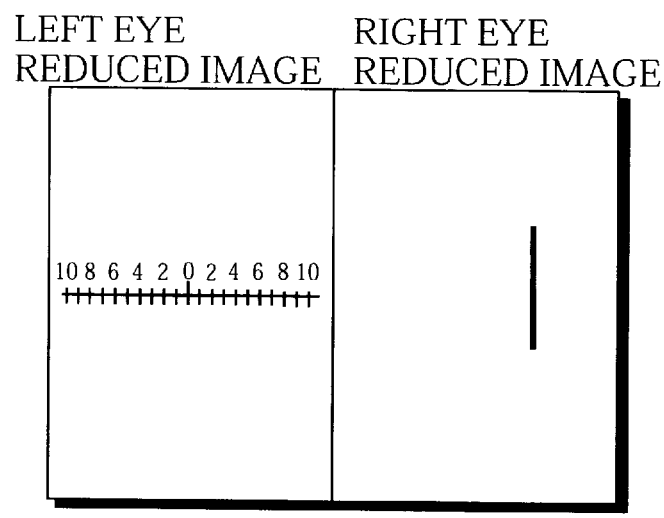
FIG. 14 is a schematic view showing a left eye reduced image corresponding to the image representing the horizontal scale displayed on the screen for an inspecting person shown in FIG. 13 and a right eye reduced image corresponding to the image representing the vertical bar displayed on the screen for an inspecting person shown in FIG. 13.

As shown in FIGS. 13 and 14, the image representing the cage 61 which is a reference image may be replaced with an image representing a horizontal scale 71, and the image representing the lion 62 which is an index image may be replaced with an image representing a vertical bar 72. FIG. 13 illustrates a screen for an inspecting person in a case where the image representing the horizontal scale 71 and the image representing the vertical bar 72 are used. FIG. 14 illustrates a left eye reduced image corresponding to the image representing the horizontal scale 71 and a right eye reduced image corresponding to the image representing the vertical bar 72 which are displayed on the screen for an inspecting person shown in FIG. 13. In this case, the amount of deviation of the image representing the vertical bar 72 from the reference position "0" of the image representing the horizontal scale 71 is displayed on the screen for an inspecting person.

Figure 15:
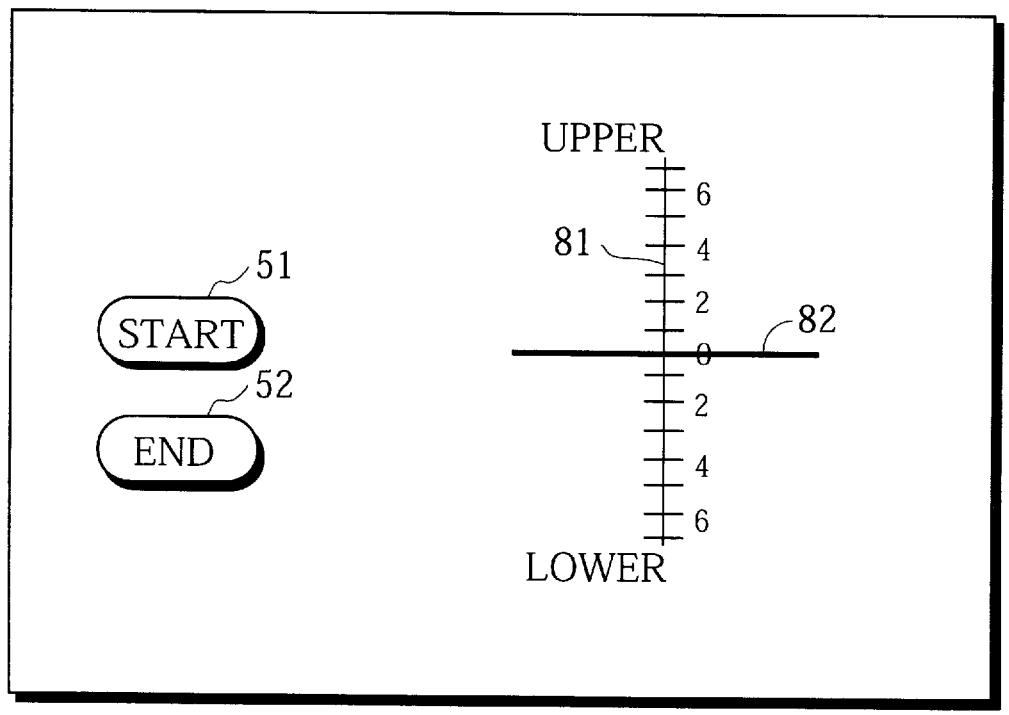
FIG. 15 illustrates one example of a screen for an inspecting person in a case where an image representing a vertical scale is used as a reference image, and an image representing a horizontal bar is used as an index image.
Figure 16:
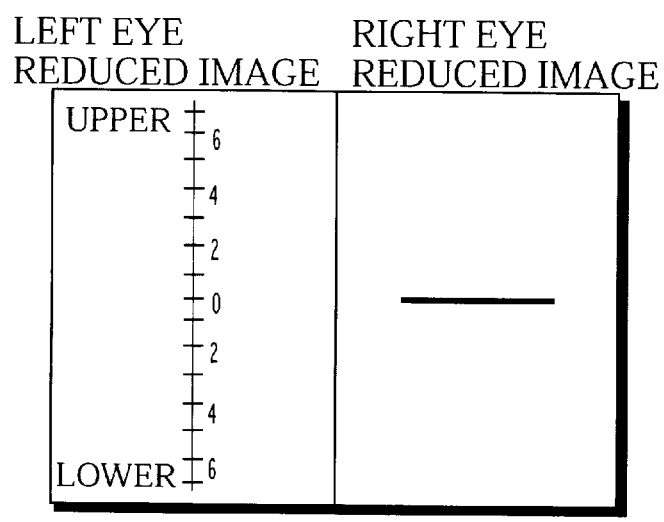
FIG. 16 is a schematic view showing a left eye reduced image corresponding to the image representing the vertical scale displayed on the screen for an inspecting person shown in FIG. 15 and a right eye reduced image corresponding to the image representing the horizontal bar displayed on the screen for an inspecting person shown in FIG. 15.

As shown in FIGS. 15 and 16, the image representing the cage 61 which is a reference image may be replaced with an image representing a vertical image 81, and the image representing the lion 62 which is an index image may be replaced with an image representing a horizontal bar 82. FIG. 15 illustrates a screen for an inspecting person in a case where the image representing the vertical scale 81 and the image representing the horizontal bar 82 are used. FIG. 16 illustrates a left eye reduced image corresponding to the image representing the vertical scale 81 and a right eye reduced image corresponding to the image representing the horizontal bar 82 which are displayed on the screen for an inspecting person shown in FIG. 15. In this case, the amount of deviation of the image representing the horizontal bar 82 from the reference position "0" of the image representing the vertical scale 81 is displayed on the screen for an inspecting person.

Figure 17:
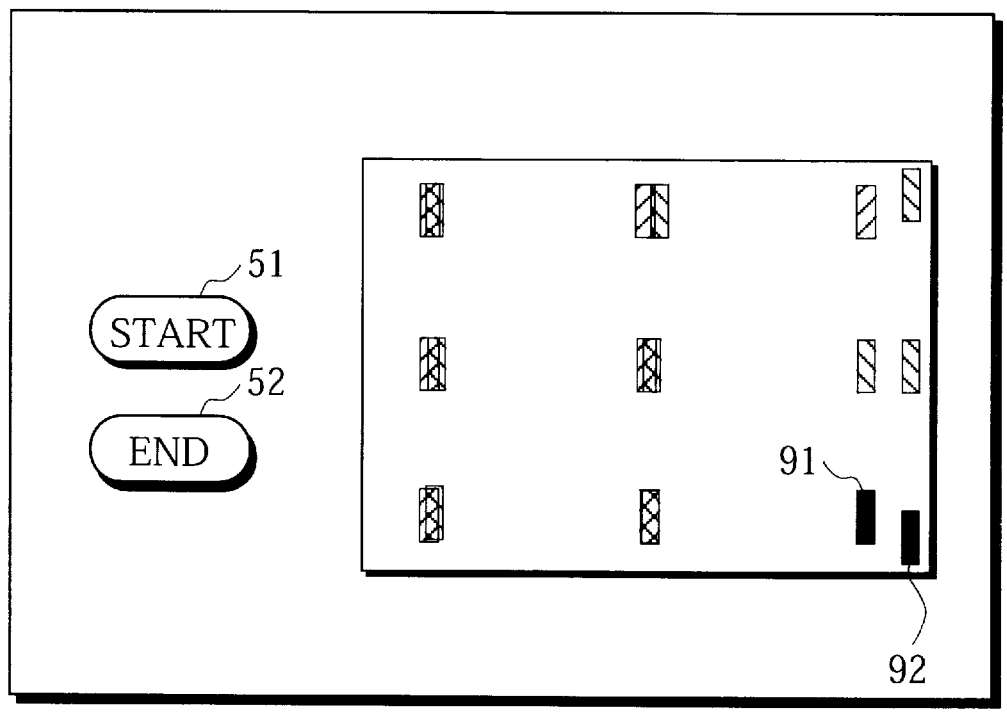
FIG. 17 illustrates one example of a screen for an inspecting person in a case where strip images are used as a reference image and an index image.
Figure 18:
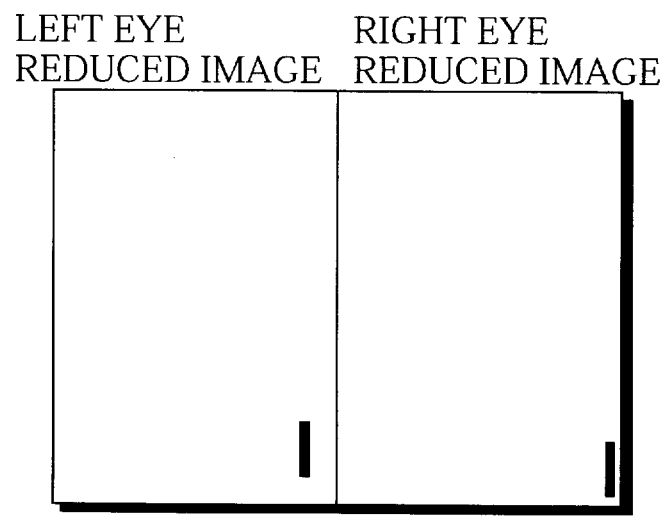
FIG. 18 is a schematic view showing a left eye reduced image corresponding to the reference image, which is being currently inspected, displayed on the screen for an inspecting person shown in FIG. 17 and a right eye reduced image corresponding to the index image, which is being currently inspected, displayed on the screen for an inspecting person shown in FIG. 17.

As shown in FIG. 17 and 18, the amount of deviation may be calculated by using a strip-shaped image 91 as a reference image and using a strip-shaped image 92 as an index image moved upon being operated by a person to be inspected, setting a plurality of display positions of the reference image within one screen, and moving the index image for each set display position.

FIG. 17 illustrates a screen for an inspecting person, which shows that the reference image 91 and the index image 92 which are hatched have been already inspected, and the reference image 91 and the index image 92 which are solid are being currently inspected. A left eye reduced image corresponding to the reference image 91 which is currently inspected and a right eye reduced image corresponding the index image 92 which is currently inspected are illustrated in FIG. 18.

Although in the above-mentioned embodiment, the display device of a parallax barrier type is used as a 3D display device, a 3D display device using no glasses such as a 3D display device of a lenticular type may be used. Further, as a 3D display device, a 3D display device using both polarizing glasses and liquid crystal shutter glasses may be used.

[2] Description of Strabismus Correcting Apparatus

The construction of hardware of a strabismus correcting apparatus is the same as the construction of the binocular view function inspecting apparatus shown in FIG. 1 and hence, the description thereof is not repeated.

Figure 19:
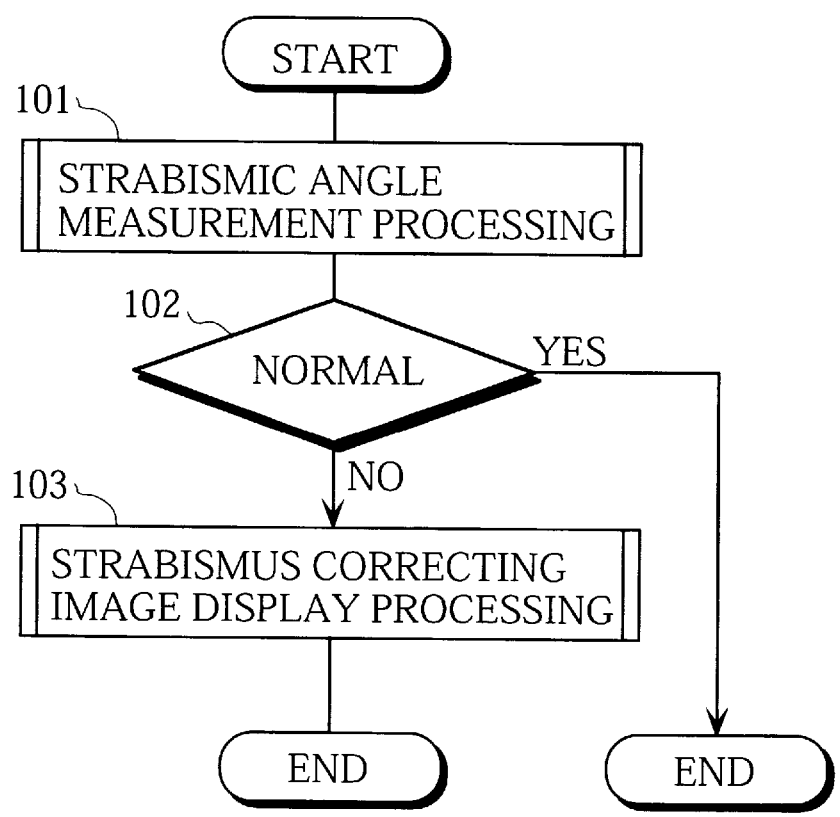
FIG. 19 is a flow chart showing the procedure for strabismus correction processing.

FIG. 19 shows the procedure for strabismus correction processing.

Strabismic angle measurement processing is first performed (step 101). It is judged whether or not a person to be inspected has a squint on the basis of information relating to a strabismic angle measured by the strabismic angle measurement processing (step 102). When it is judged that the person to be inspected does not have a squint, that is, it is judged that the person to be inspected is normal, no correction is required, whereby the current processing is terminated. When it is judged that the person to be inspected has a squint, that is, it is judged that the person to be inspected is not normal, strabismus correcting image display processing is performed (step 103).

Figure 20:
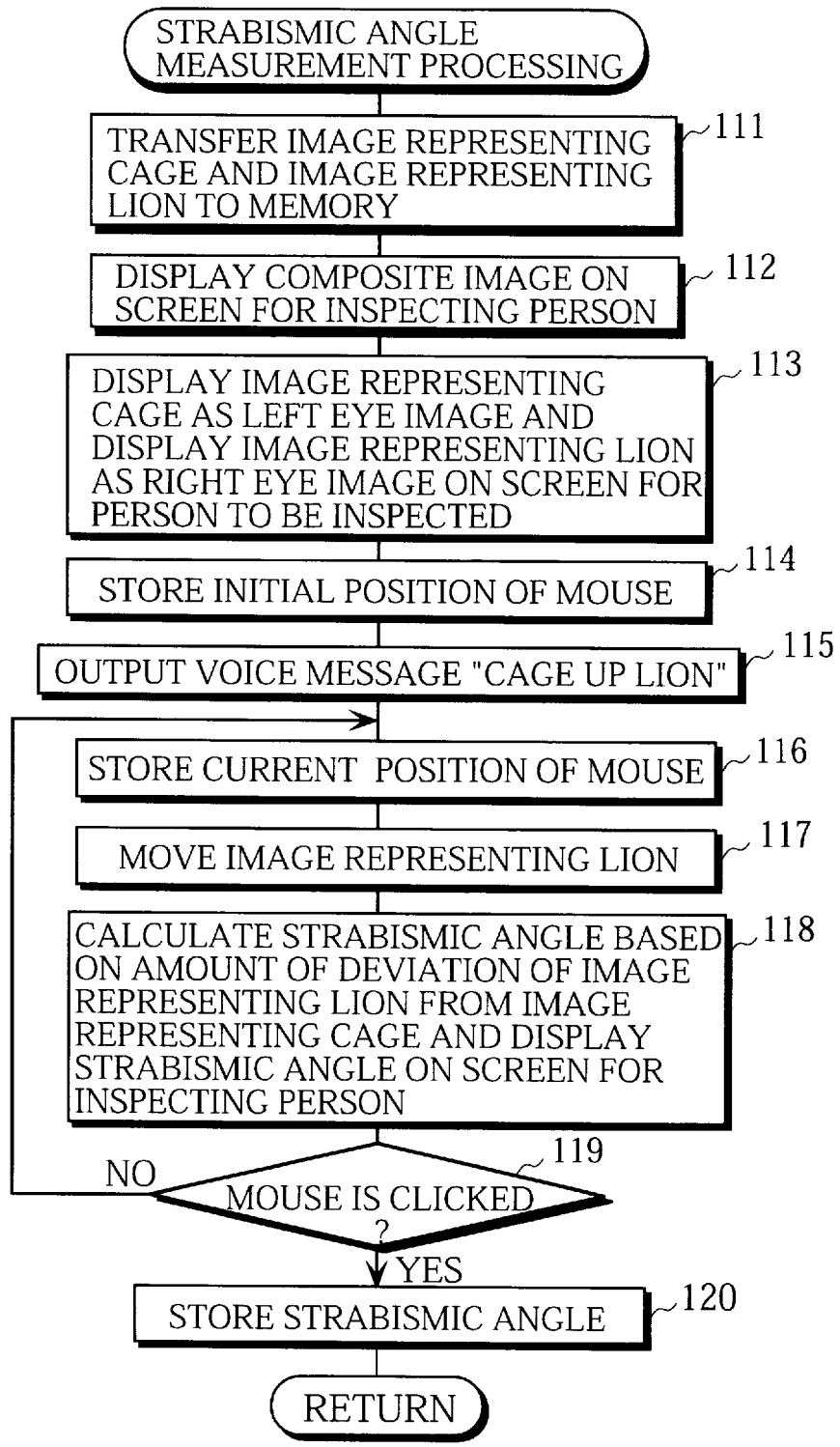
FIG. 20 is a flow chart showing the detailed procedure for strabismic angle measurement processing in the step 101 shown in FIG. 19.

FIG. 20 shows the detailed procedure for the strabismic angle measurement processing in the step 101 shown in FIG. 19.

An image representing a cage serving as a reference image shown in FIG. 6, an image representing a lion serving as an index image shown in FIG. 7, and a strabismus correcting image (not shown) are stored in a hard disk 12. FIG. 8 illustrates one example of an initial screen displayed on a 2D display 19 (hereinafter referred to as a screen for an inspecting person). A start button 51 and an end button 52 are displayed on the initial screen.

When the start button 51 is pushed, the image representing the cage and the image representing the lion are read out from the hard disk 12, and are stored in a memory 13 (step 111). Their composite image is sent to the 2D display 19 through a frame memory 15 and a D/A converter 17, and is displayed on the 2D display 19 (step 112). One example of the image is illustrated in FIG. 9.

In this example, an image representing a cage 61 and an image representing a lion 62 are displayed in addition to the start button 51 and the end button 52, and their horizontal deviation and their vertical deviation are displayed.

On the other hand, the image representing the cage and the image representing the lion which are stored in the memory 13 are taken as a left eye image and a right eye image and are reduced to one-half in the horizontal direction, respectively, to produce an image corresponding to one frame. One example of a left eye reduced image and a right eye reduced image respectively corresponding to the images representing the cage and the lion which are displayed on the screen for an inspecting person shown in FIG. 9 is illustrated in FIG. 10. The produced image corresponding to one frame is sent to a 3D display device 2 through a frame memory 16 and a D/A converter 18.

The 3D display device 2 respectively decomposes the left eye reduced image and the right eye reduced image which are sent into longwise strip-shaped images, alternately arranges the left eye strip-shaped images and the right eye strip-shaped images in the horizontal direction and displays the images on a liquid crystal panel 41 (hereinafter referred to as a screen for a person to be inspected) (step 113). Consequently, the same images as the images displayed on the screen for an inspecting person, that is, the image representing the cage and the image representing the lion are displayed on the screen for a person to be inspected. Only the image representing the cage and only the image representing the lion are respectively seen with the left eye and the right eye of a person to be inspected.

Furthermore, the initial position of a mouse is stored in the memory 13 (step 114). Thereafter, a voice message "Cage a lion" is outputted from a speaker 20 (step 115).

An operator so operates the mouse (included in an input device 14) that the lion is caged, and clicks the mouse when the lion has been caged.

When the mouse is operated, the current position of the mouse is stored in the memory 13 (step 116). The image representing the lion is moved on the screen for an inspecting person and the screen for a person to be inspected on the basis of the direction in which the mouse is moved and the amount of movement thereof (step 117). A new image displayed on the screen for an inspecting person and a new image sent to the 3D display device 2 are produced on the basis of the image representing the cage and the image representing the lion which are stored in the memory 13.

Strabismic angles in the horizontal direction and the vertical direction between the image representing the cage and the image representing the lion are calculated on the basis of the direction in which the mouse is moved and the amount of movement thereof, and the calculated strabismic angles are displayed on the screen for an inspecting person (step 118). The program is returned to the step 102 shown in FIG. 9.

Until the mouse is clicked, the processing in the steps 116 to 118 is repeatedly performed. When the mouse is clicked, the answer is in the affirmative in the step 119, after which the program proceeds to the step 120. In the step 120, the strabismic angles in the horizontal direction and the vertical direction which are finally calculated are stored in the hard disk 12. One example of the screen for an inspecting person in a case where the mouse is clicked is shown in FIG. 11. Further, a left eye reduced image and a right eye reduced image respectively corresponding to the images representing the cage and the lion which are displayed on the screen for an inspecting person shown in FIG. 11 are illustrated in FIG. 12.

In the step 102 shown in FIG. 19, it is judged whether or not the strabismic angles measured in the strabismic angle measurement processing in the step 101 are within an allowable angle. If the strabismic angles are within the allowable range, no strabismus correction is required, whereby the current processing is terminated. If the strabismic angles are outside the allowable range, the program proceeds to strabismus correcting image display processing in the step 103.

Figure 21:
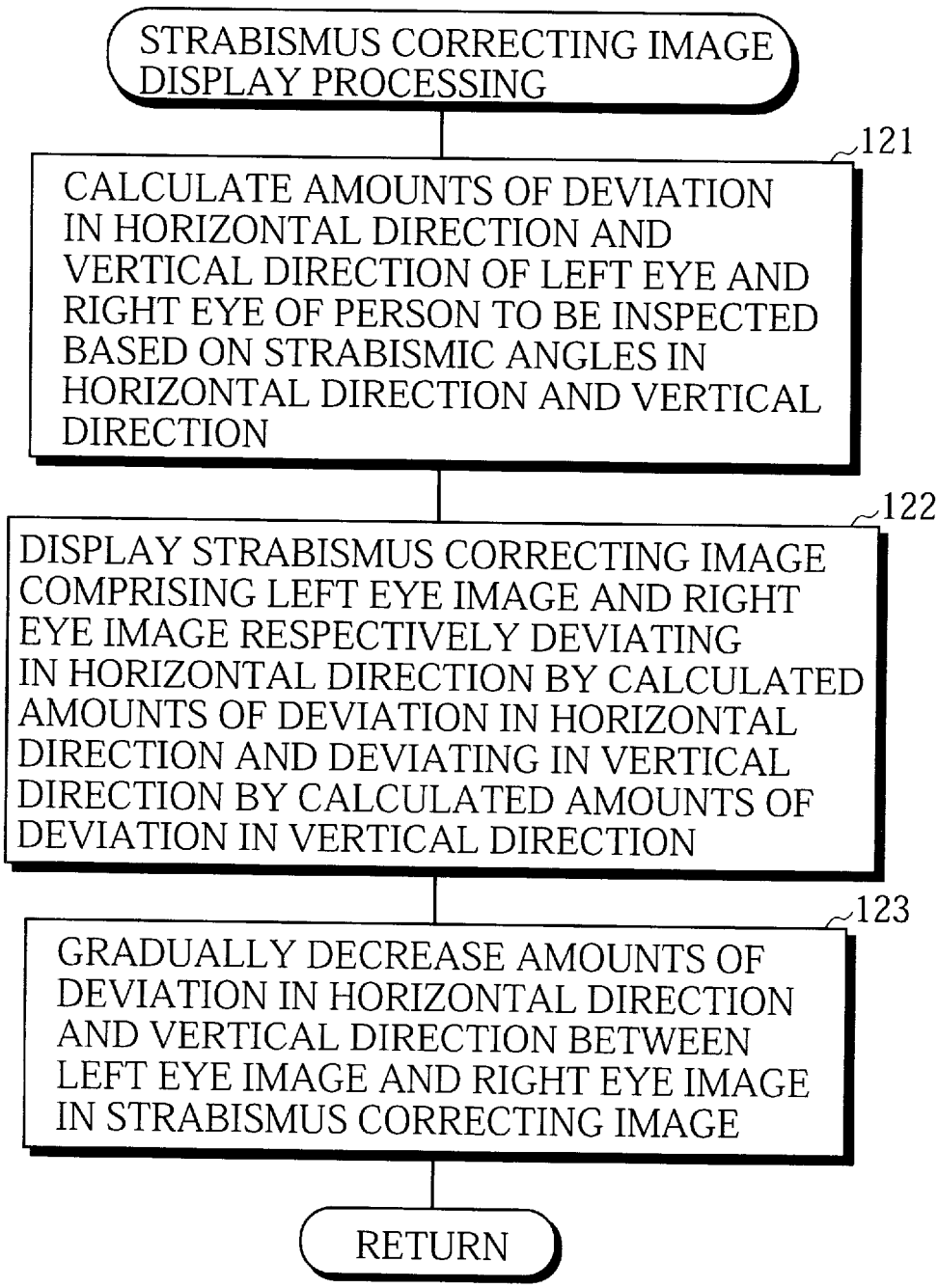
FIG. 21 is a flow chart showing the detailed procedure for display processing of a strabismus correcting image in the step 103 shown in FIG. 19.

FIG. 21 shows the detailed procedure for the strabismus correcting image display processing in the step 103 shown in FIG. 19.

First, the amounts of deviation in the horizontal direction of the left eye and the right eye of the person to be inspected are calculated on the basis of the strabismic angle in the horizontal direction, and the amounts of deviation in the vertical direction of the left eye and the right eye of the person to be inspected are calculated on the basis of the strabismic angle in the vertical direction (step 121).

A strabismus correcting image comprising a left eye image and a right eye image which respectively deviate in the horizontal direction by the calculated amounts of deviation in the horizontal direction and respectively deviate in the vertical direction by the calculated amounts of deviation in the vertical direction is displayed on the 3D display device 2 (step 122).

Specifically, the strabismus correcting image is first read out from the hard disk 12, and is stored in the memory 13. A left eye image and a right eye image which respectively deviate in the horizontal direction by the amounts of deviation in the horizontal direction calculated in the step 122 and respectively deviate in the vertical direction by the amounts of deviation in the vertical direction calculated in the step 122 are produced from the strabismus correcting image stored in the memory 13, and are respectively reduced to one-half in the horizontal direction, to produce an image corresponding to one frame. The produced image corresponding to one frame is sent to the 3D display device 2 through the frame memory 16 and the D/A converter 18.

Figures 22A, 22B, 22C:
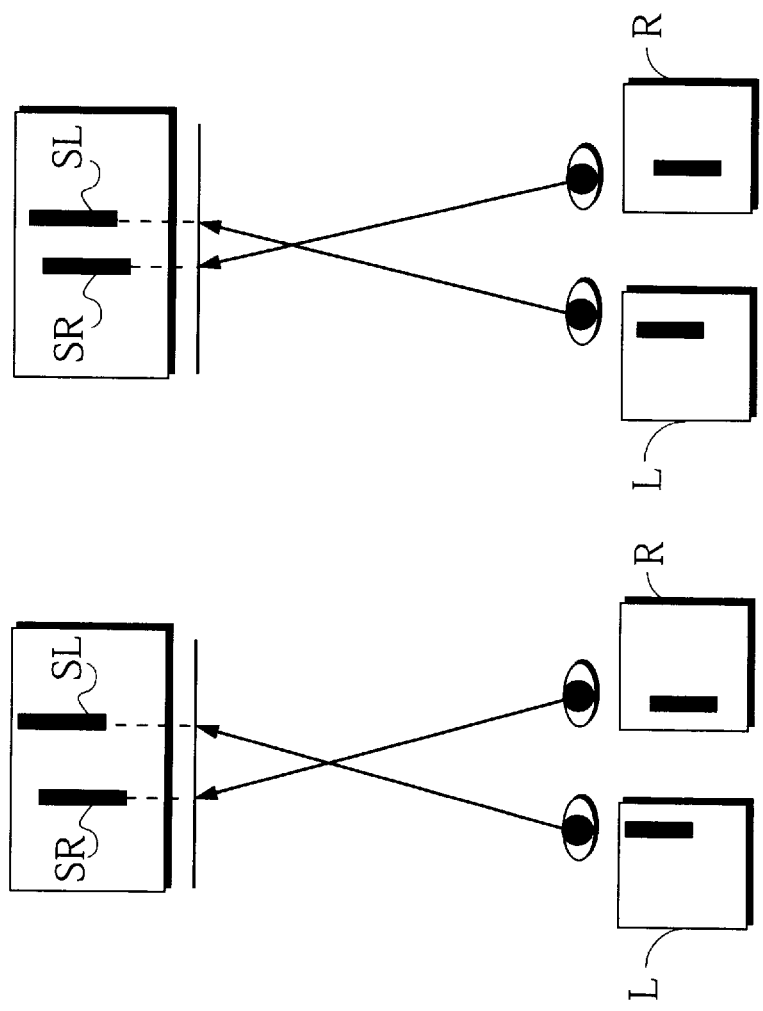
FIGS. 22a, 22b and 22c are schematic views showing an example of display of the strabismus correcting image.
Figure 23:
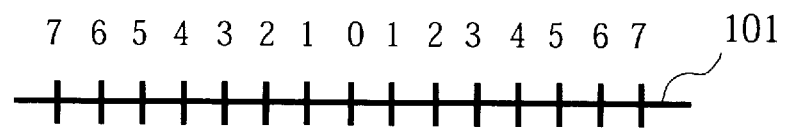
FIG. 23 is a schematic view showing a horizontal scale used for a conventional Maddox test.
Figure 24:
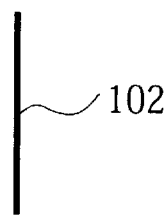
FIG. 24 is a schematic view showing a vertical bar used for a conventional Maddox test.
Figure 25:
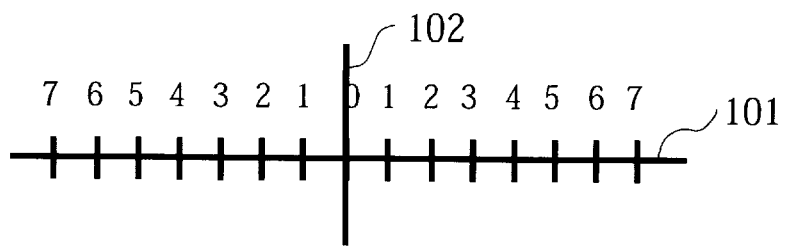
FIG. 25 is a schematic view showing an image visually recognized by a person to be inspected when the person to be inspected is normal.
Figure 26:
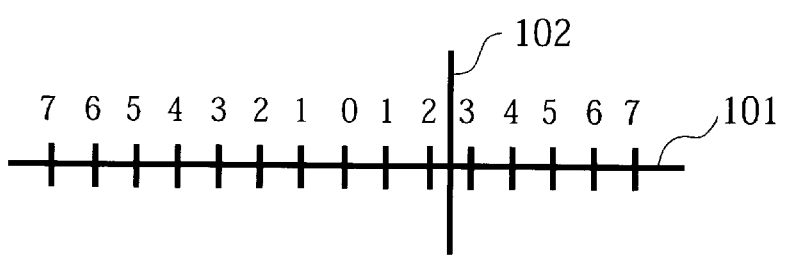
FIG. 26 is a schematic view showing an image visually recognized by a person to be inspected when the person to be inspected has a squint.

The 3D display device 2 respectively decomposes the left eye reduced image and the right eye reduced image which are sent into longwise strip-shaped images, alternately arranges the left eye strip-shaped images and the right eye strip-shaped images in the horizontal direction and displays the images on the liquid crystal panel 41 (hereinafter referred to as a screen for a person to be inspected). FIG. 22a illustrates the left eye image L and the right eye image R in this case and the strabismus correcting image displayed on the 3D display device 2.

The person to be inspected views an index SL included in the left eye strabismus correcting image displayed on the 3D display device 2 with the left eye, and views an index SR included in the right eye strabismus correcting image with the right eye.

Thereafter, the amounts of deviation in the horizontal direction and the vertical direction between the left eye image and the right eye image in the strabismus correcting image displayed on the 3D display device 2 are gradually decreased (step 123). Specifically, the left eye image and the right eye image are so produced that the amounts of deviation in the horizontal direction and the vertical direction are gradually decreased, and are displayed on the 3D display device 2. Consequently, the left eye image and the right eye image in a case where the amounts of deviation in the horizontal direction and the vertical direction therebetween are zero are finally produced, and are displayed on the 3D display device 2.

FIG. 22b illustrates a left eye image L and a right eye image R in a case where the amounts of deviation therebetween are decreased and a strabismus correcting image displayed on the 3D display device 2. FIG. 22c illustrates a left eye image L and a right eye image R in a case where the amounts of deviation therebetween are zero and a strabismus correcting image displayed on the 3D display device 2.

The person to be inspected first views the left eye image and the right eye image which have an amount of deviation corresponding to his or her own strabismic angle, whereby an image caught by the left eye and an image caught by the right eye are so seen that they coincide with each other. The amount of deviation between the left eye image and the right eye image is so gradually decreased as to be close to zero which is a normal value, whereby the person to be inspected attempts to so unconsciously catch the left eye image and the right eye image that they coincide with each other. The strabismus is corrected by such an unconscious function.

It is preferable that as the strabismus correcting image, a moving image is used in order that the person to be inspected can continue to view the image with interest.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A binocular view function inspecting apparatus comprising:

display means for displaying a reference image and an index image on a three-dimensional display device with either one of the images taken as a left eye image and the other image taken as a right eye image;

first input means for causing a person to be inspected to input a movement command to move a display position of the index image in order that a predetermined reference position of the reference image and the display position of the index image coincide with each other;

index image movement means for moving the display position of the index image on the basis of the movement command from the first input means;

second input means for causing the person to be inspected to provide, when the person to be inspected visually recognizes that the reference position of the reference image and the display position of the index image coincide with each other, confirmation input indicating that the person to be inspected visually recognizes the coincidence; and calculation means for calculating the amount of deviation of the index image from the reference position of the reference image when the confirmation input is provided.

2. The binocular view function inspecting apparatus according to claim 1, further comprising judgment means for judging whether or not the person to be inspected is normal on the basis of the amount of deviation calculated by the calculation means, and reporting means for reporting the results of the judgment by the judgment means to an inspecting person.

3. A binocular view function inspecting method comprising:

a first step of displaying a reference image and an index image on a three-dimensional display device with either one of the images taken as a left eye image and the other image taken as a right eye image;

a second step of causing a person to be inspected to input a movement command to move a display position of the index image in order that a predetermined reference position of the reference image and the display position of the index image coincide with each other;

a third step of moving the display position of the index image on the basis of the inputted movement command;

a fourth step of causing the person to be inspected to provide, when the person to be inspected visually recognizes that the reference position of the reference image and the display position of the index image coincide with each other, confirmation input indicating that the person to be inspected visually recognizes the coincidence; and a fifth step of calculating the amount of deviation of the index image from the reference position of the reference image when the confirmation input is provided.

4. The binocular view function inspecting method according to claim 3, further comprising a sixth step of judging whether or not the person to be inspected is normal on the basis of the amount of deviation calculated in the fifth step, and a seventh step of reporting the results of the judgment in the sixth step to an inspecting person.

5. A computer readable recording medium on which a binocular view function inspecting program is recorded, said program causing a computer to carry out the following steps:

displaying a reference image and an index image on a three-dimensional display device with either one of the images taken as a left eye image and the other image taken as a right eye image;

moving a display position of the index image, when a movement command to move the display position of the index image is inputted by a person to be inspected in order that a predetermined reference position of the reference image and the display position of the index image coincide with each other, on the basis of the movement command; and calculating the amount of deviation of the index image from the reference position of the reference image by the person to be inspected visually recognizing that the reference position of the reference image and the display position of the index image coincide with each other when confirmation input indicating that the person to be inspected visually recognizes the coincidence is provided by the person to be inspected.

6. A strabismus correcting apparatus comprising a strabismic angle measurement means for measuring information relating to the strabismic angle of a person to be inspected, and strabismus correcting means for displaying a strabismus correcting image comprising a left eye image and a right eye image on a three-dimensional display device on the basis of the information relating to the strabismic angle measured by the strabismic angle measurement means, the strabismus correcting means comprising means for displaying the strabismus correcting image comprising the left eye image and the right eye image which have an amount of deviation corresponding to the strabismic angle of the person to be inspected on the three-dimensional display device, and means for gradually decreasing the amount of deviation between the left eye image and the right eye image in the strabismus correcting image displayed on the three-dimensional display device.

7. The strabismus correcting apparatus according to claim 6, wherein the strabismic angle measurement means comprises display means for displaying a reference image and an index image on the three-dimensional display device with either one of the images taken as a left eye image and the other image taken as a right eye image, first input means for causing the person to be inspected to input a movement command to move a display position of the index image in order that a predetermined reference position of the reference image and the display position of the index image coincide with each other, index image movement means for moving the display position of the index image on the basis of the movement command from the first input means, second input means for causing the person to be inspected to provide, when the person to be inspected visually recognizes that the reference position of the reference image and the display position of the index image coincide with each other, confirmation input indicating that the person to be inspected visually recognizes the coincidence, and calculation means for calculating the amount of deviation of the index image from the reference position of the reference image when the confirmation input is provided, to obtain information relating to the strabismic angle of the person to be inspected.

8. The strabismus correcting apparatus according to claim 7, wherein the strabismus correcting image is a moving image.

9. The strabismus correcting apparatus according to claim 6, wherein the strabismus correcting image is a moving image.

10. A strabismus correcting method comprising a strabismic angle measuring step of measuring information relating to the strabismic angle of a person to be inspected, and a strabismus correcting step of displaying a strabismus correcting image comprising a left eye image and a right eye image on a three-dimensional display device on the basis of the information relating to the strabismic angle measured by the strabismic angle measuring step, the strabismus correcting step comprising the step of displaying the strabismus correcting image comprising the left eye image and the right eye image which have an amount of deviation corresponding to the strabismic angle of the person to be inspected on the three-dimensional display device, and the step of gradually decreasing the amount of deviation between the left eye image and the right eye image in the strabismus correcting image displayed on the three-dimensional display device.

11. The strabismus correcting method according to claim 10, wherein the strabismic angle measuring step comprises a first step of displaying a reference image and an index image on the three-dimensional display device with either one of the images taken as a left eye image and the other image taken as a right eye image, a second step of causing the person to be inspected to input a movement command to move a display position of the index image in order that a predetermined reference position of the reference image and the display position of the index image coincide with each other, a third step of moving the display position of the index image on the basis of the movement command from the first input means, a fourth step of causing the person to be inspected to provide, when the person to be inspected visually recognizes that the reference position of the reference image and the display position of the index image coincide with each other, confirmation input indicating that the person to be inspected visually recognizes the coincidence, and a fifth step of calculating the amount of deviation of the index image from the reference position of the reference image when the confirmation input is provided, to obtain information relating to the strabismic angle of the person to be inspected.

12. The strabismus correcting method according to claim 11, wherein the strabismus correcting image is a moving image.

13. The strabismus correcting method according to claim 10, wherein the strabismus correcting image is a moving image.

14. A computer readable recording medium on which a strabismus correcting program is recorded, said program causing a computer to carry out a strabismic angle measuring step of measuring information relating to the strabismic angle of a person to be inspected, and a strabismus correcting step of displaying a strabismus correcting image comprising a left eye image and a right eye image on a three-dimensional display device on the basis of the information relating to the strabismic angle measured by the strabismic angle measuring step, the strabismus correcting step comprising the step of displaying the strabismus correcting image comprising the left eye image and the right eye image which have an amount of deviation corresponding to the strabismic angle of the person to be inspected on the three-dimensional display device, and the step of gradually decreasing the amount of deviation between the left eye image and the right eye image in the strabismus correcting image displayed on the three-dimensional display device.

15. A computer readable recording medium on which the strabismus correcting program as set forth in the claim 14 is recorded, wherein the strabismic angle measuring step comprises the steps of displaying a reference image and an index image on the three-dimensional display device with either one of the images taken as a left eye image and the other image taken as a right eye image, moving a display position of the index image, when a movement command to move the display position of the index image is inputted by a person to be inspected in order that a predetermined reference position of the reference image and the display position of the index image coincide with each other, on the basis of the movement command, calculating the amount of deviation of the index image from the reference position of the reference image by the person to be inspected visually recognizing that the reference position of the reference image and the display position of the index image coincide with each other when confirmation input indicating that the person to be inspected visually recognizes the coincidence is provided by the person to be inspected.

16. A computer readable recording medium on which the strabismus correcting program as set forth in the claim 15 is recorded, wherein the strabismus correcting image is a moving image.

17. A computer readable recording medium on which the strabismus correcting program as set forth in the claim 14 is recorded, wherein the strabismus correcting image is a moving image.

* * * * *